United States Patent
Barraza et al.

(10) Patent No.: US 10,342,841 B2
(45) Date of Patent: *Jul. 9, 2019

(54) USE OF AN ORGANIC CITRUS EXTRACT WITH HIGH ANTIMICROBIAL CAPACITY AND XYLITOL AS A PRESERVATIVE SYSTEM IN LIQUIDS, EMULSIONS, SUSPENSIONS, CREAMS AND ANTACIDS

(71) Applicant: JOHNSON & JOHNSON CONSUMER INC., Skillman, NJ (US)

(72) Inventors: Javier Barraza, São José dos Campos (BR); Renata Muniz, São José dos Campos (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/165,275

(22) Filed: May 26, 2016

(65) Prior Publication Data

US 2016/0346341 A1    Dec. 1, 2016

Related U.S. Application Data

(60) Provisional application No. 62/168,002, filed on May 29, 2015.

(51) Int. Cl.

| | |
|---|---|
| A61K 9/00 | (2006.01) |
| A61K 36/752 | (2006.01) |
| A61K 33/08 | (2006.01) |
| A61K 47/26 | (2006.01) |
| A61K 47/14 | (2017.01) |
| A61K 45/06 | (2006.01) |
| A61K 47/34 | (2017.01) |
| A61K 47/46 | (2006.01) |
| A61K 31/047 | (2006.01) |
| A61K 31/341 | (2006.01) |
| A61K 31/4164 | (2006.01) |
| A61K 31/426 | (2006.01) |
| A61K 31/80 | (2006.01) |

(52) U.S. Cl.
CPC .......... *A61K 36/752* (2013.01); *A61K 9/0053* (2013.01); *A61K 9/0095* (2013.01); *A61K 31/047* (2013.01); *A61K 31/341* (2013.01); *A61K 31/4164* (2013.01); *A61K 31/426* (2013.01); *A61K 31/80* (2013.01); *A61K 33/08* (2013.01); *A61K 45/06* (2013.01); *A61K 47/14* (2013.01); *A61K 47/26* (2013.01); *A61K 47/34* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 5,229,137 A | 7/1993 | Wolfe | |
| 5,455,050 A | 10/1995 | Beyerle et al. | |
| 5,496,567 A | 3/1996 | McLean | |
| 5,498,426 A | 3/1996 | Wilson et al. | |
| 5,874,112 A | 2/1999 | McNally et al. | |
| 5,914,135 A | 6/1999 | Dubek et al. | |
| 5,976,578 A | 11/1999 | Beyerle et al. | |
| 7,399,772 B2 * | 7/2008 | Phillips | A61K 9/0007 514/338 |
| 8,859,018 B2 | 10/2014 | Gehin-Delval et al. | |
| 2003/0215525 A1 | 11/2003 | Beyerle et al. | |
| 2006/0216246 A1 | 9/2006 | Belanger et al. | |
| 2008/0193531 A1 * | 8/2008 | Hermelin | A61K 9/2013 424/474 |
| 2010/0323043 A1 | 12/2010 | Perla et al. | |
| 2012/0100231 A1 | 4/2012 | Perla et al. | |
| 2014/0322147 A1 | 10/2014 | Modak et al. | |
| 2017/0079281 A1 * | 3/2017 | Methot | A01N 65/36 |

FOREIGN PATENT DOCUMENTS

| | | |
|---|---|---|
| CA | 2179682 | 2/1997 |
| FR | 2595249 A1 | 9/1987 |
| WO | WO 92/00102 | 1/1992 |
| WO | WO 9510290 A1 | 4/1995 |
| WO | WO 1998014200 A1 | 4/1998 |
| WO | WO 2001045725 A2 | 6/2001 |
| WO | WO 2014060990 A1 | 4/2014 |

OTHER PUBLICATIONS

"Microbiological Stability of Oral Dosage Forms, Problems with Liquid Antacids", S.T.P. Pharma, 1 (8) 720-726 (1985).
"Preservative-Free and Self-Preserving Cosmetics and Drugs", Ed. J. J. Kabara and D. S. Orth, pp. 245-246 (1996).
"A Comparative Study of the Effectiveness of Preservatives in Twelve Antacid Suspensions" Drug Development and Industrial Pharmacy, 13(8), 1429-1446 (1987).
Milgrom P., Ly K. A., Rothen M., Research findings on xylitol and the development of xylitol vehicles to address public health needs, National Center for Biotechnology Information, NIH Public Access, Author Manuscript, available online on Jul. 2009.
Mäkinen K. M., Eva S., Effect of Xylitol on some Food-Spoilage Microorganisms, Journal of Food Science, 46:950-951, 2006.
Soderling E., Hirvonen A., Karjalainen S., Fontana M., Catt D., Seppa L., The effect of Xylitol on the composition of the oral flora: A Pilot Study, European Journal of Dentistry, vol. 5, January 201, pp. 24-31.
Aksoy A, Nizami D., Koksal F. , In vitro and in vivo antimicrobial effects of mastic chewing gum against *Streptococcus mutans* and mutans streptococci, Archives of Oral Biology, vol. 51, Issue 6, Jun. 2006, pp. 47-481.
Rowe. C. R., Sheskey J. P., Quinn E. M., Handbook of Pharmaceutical Excipients, Sixth Edition, Pharmaceutical Press, 2009, ISBN 978-0-85369-792-3.
Costerton, J.W.; Lewandowski, Z.; Caldwell, D.E.; Korber, D.R.; Lappin-Socott, H.M. Microbial Biofilms. Ann. Rev. Microbiol, v. 49.p. 711-745, 1995.

(Continued)

*Primary Examiner* — Susan T Tran
(74) *Attorney, Agent, or Firm* — Laura A. Donnelly

(57) ABSTRACT

Liquid antacid compositions containing *citrus* extract are disclosed. The liquid antacid compositions possess superior resistance to microbial attack.

11 Claims, No Drawings

(56) References Cited

OTHER PUBLICATIONS

Katsuyama M, Masako K, Ichikawa H, et al. A novel method to control the balance of skin microflora. Part 1. Attack on biofilm of *Staphylococcus aureus* without antibiotics, J Dermatol Sci 2005; 38(3):197-205.

"Safety assessment of esters of p-hydroxybenzoic acid (parabens)", M.G. Soni , I.G. Carabin , G.A. Burdock, Food and Chemical Toxicology 43 (2005) 985-1015.

United States Environmental Protection Agency http://www.epa.gov/airtoxics/hlthef/phenol.html.

Woedtke Von T et al: "Aspects of the Antimicrobial Efficacy of Grapefruit Seed Extract and Its Relation to Preservative Substances Contained", Pharmazie,, vol. 54, No. 6, Jun. 1, 1999 (Jun. 1, 1999), pp. 452-456, XP001247017, ISSN: 0031-7144 abstract; table 1.

International Search Report dated Aug. 11, 2016 for PCT/US2016/034376.

Database WPI, Week 200007. Thompson Scientific, London, GB; AN 2000-075369. XP002760513 & JP H11310524A (Taisho Pharm Co. Ltd). Nov. 9, 1999. abstract.

International Search Report dated Aug. 12, 2016 for PCT/US2016/034368.

\* cited by examiner

USE OF AN ORGANIC CITRUS EXTRACT WITH HIGH ANTIMICROBIAL CAPACITY AND XYLITOL AS A PRESERVATIVE SYSTEM IN LIQUIDS, EMULSIONS, SUSPENSIONS, CREAMS AND ANTACIDS

This application claims priority of the benefit of the filing of U.S. Provisional Application Ser. No. 62/168,002, filed May 29, 2015, the contents of which are hereby incorporated by reference in their entirety.

BACKGROUND OF THE INVENTION

Field of the Invention

The present invention relates to liquid antacid compositions and methods for their preparation. More particularly, the present invention relates to liquid antacid compositions containing *citrus* extract and xylitol. The compositions have enhanced resistance to microbial contamination.

Description of the Related Art

Antacids are widely used in the treatment of various gastrointestinal disorders such as peptic ulcers and gastritis. Antacids are also used for the relief of acid indigestion, heartburn, dyspepsia, sour stomach, reflux esophagitis and the like. The clinical use of antacids is based on their ability to neutralize stomach acid and increase the pH of gastric secretions. Although antacids do not neutralize all gastric acid, increasing gastric pH from 1.3 to 2.3 neutralizes 90% of gastric acid and increasing gastric pH to 3.3 neutralizes 99% of gastric acid. For optimal healing of peptic ulcers, most clinicians believe that gastric pH should be maintained at about 3-3.5. Accordingly, it is desirable that an antacid feature a high acid neutralization capacity and a rapid rate of gastric acid neutralization.

Antacids used today are made from a variety of inorganic salts such as calcium carbonate, sodium bicarbonate, magnesium salts and aluminum salts. Magnesium hydroxide and aluminum hydroxide, which are the most potent magnesium and aluminum compounds, are often used in combination. In addition, magnesium oxide, magnesium carbonate, aluminum phosphate, magaldrate and magnesium trisilicate are also employed.

Antacids are available in both liquid suspensions as well as solid dosage forms, e.g., tablets and powders. In general, liquid suspensions are preferred since they are more rapidly and effectively solubilized and have a greater ability to react with and neutralize gastric acid.

One concern with liquid antacid compositions is the lack of patient compliance due to poor taste of antacid actives and the bitterness of preservatives that are often added. Another concern is the fact that liquid antacid compositions are generally susceptible to microbial contamination. "Microbiological Stability of Oral Dosage Forms, Problems with Liquid Antacids", S.T.P. Pharma, 1 (8) 720-726 (1985). Maintaining proper pH of an aqueous based solution aids in controlling the microbial growth in the solution. Generally, acidic solutions (below about pH 4.5) or alkaline solutions (above about pH 9.5) are less susceptible to microbial growth than neutral solutions (about pH 6-9). "Preservative-Free and Self-Preserving Cosmetics and Drugs", Ed. J. J. Kabara and D. S. Orth, pages 245-246 (1996). Although under most circumstances microbial growth can be restricted with preservative, the pH of the finished product can affect degradation of the preservative. Another advantage of the invention is the avoidance of interaction between some flavors and parabens.

Sorbates such as potassium sorbate or calcium sorbate are typically used as preservatives in liquid pharmaceutical products. Potassium sorbate and calcium sorbate are slightly soluble in water and more soluble at a pH below their pKa value, for instance less than a pH of about 5. Antacid liquids have a pH which is much higher (greater than about 7.0). Sorbates are less soluble in antacid formulations and therefore less effective for use as preservatives. There is a need for preservatives that are natural and effective at high pH levels in liquid formulations.

Although alkyl esters of parahydroxybenzoic acid (i.e., parabens, e.g., butylparaben, methylparaben and propylparaben) are often used as preservatives, they degrade over time and this degradation process increases exponentially with an increase in pH. "A Comparative Study of the Effectiveness of Preservatives in Twelve Antacid Suspensions" Drug Development and Industrial Pharmacy, 13(8), 1429-1446 (1987). Consequently, in order to achieve adequate preservative levels throughout the shelf life of a product with an alkaline pH, higher levels of the preservative must be added. Alternatively, in some instances combinations of various parabens such as methylparaben, propylparaben and butylparaben may be employed to mitigate the degradation of any one paraben; which can further affect the taste of the product. This can affect the taste of the finished product.

It is known that parabens suffer hydrolysis in alkaline pH environments such as those required to neutralize gastric acid. Hydrolysis of parabens produces phenol, which is believed to be hazardous for human health. In response, consumers have asked that consumer companies remove or limit parabens from their products.

Additionally, parabens are known to be adsorbed onto and bind with plastic containers over time, which can lead to loss within the formula and potential loss of effectiveness as a preservative.

In some cases the real-life use of antacid products by some consumers can contribute to microbial propagation within formulas and on package surfaces. Consumers and patients are known to utilize antacid bottle packaging as a direct dosing apparatus, without the use of a syringe or dosing cup. This type of behavior can accelerate the growth of microbes, emphasizing the need for an effective preservative system.

Accordingly, there is a need for a preservative system for liquid antacid compositions that effectively inhibits microbial contamination over the shelf life of the product without adversely affecting the taste of the finished product.

U.S. Pat. No. 5,455,050 to McNeil-PPC, Inc. discloses the use of buffering agents such as citric acid and tartaric acid in calcium carbonate/magnesium salt antacid suspensions to lower pH to inhibit degradation of preservative.

U.S. Pat. No. 5,498,426 to Proctor & Gamble Company discloses liquid antacid compositions that comprise an alkaline earth carbonate salt, e.g., calcium carbonate, an alkali metal phosphate salt, e.g., potassium phosphate, and an alkali metal bicarbonate salt, e.g., potassium bicarbonate.

U.S. Pat. No. 5,496,567 to McLean discloses a liquid pharmaceutical composition having buffering properties that comprises calcium carbonate ($CaCO_3$) and magnesium oxide (MgO; magnesia) or magnesium hydroxide ($Mg(OH)_2$).

U.S. Pat. No. 5,874,112 to McNeil PPC-Inc. discloses a translucent antacid composition formed by an aqueous colloidal aluminum hydroxide gel, wherein the average particle size of the aluminum hydroxide is less than about 0.5 microns.

U.S. Pat. No. 5,914,135 to McNeil-PPC, Inc. discloses calcium carbonate liquid antacid compositions containing one or more pH adjusting agents to maintain the pH above 9.0.

U.S. Pat. No. 5,976,578 to McNeil-PPC, Inc. discloses liquid antacid compositions containing a tri- or di-ester buffer such as triacetin.

Canadian Patent No. CA2179682 to Rhone Poulenc discloses an antacid composition that contains an antacid active, a sugar or sugar alcohol, and a pharmaceutically harmless solvent.

International Application No. WO9510290 to Warner Lambert discloses antacid compositions that contain a dual or tripartite combination of calcium carbonate, calcium or magnesium citrate and/or calcium phosphate.

SUMMARY OF THE INVENTION

The invention relates to liquid antacid compositions that contain citrus extract having superior resistance to microbial contamination.

The citrus extract may be combined with other preservatives in order to improve the antimicrobial effectiveness test. In one embodiment, xylitol may be added to the suspension to prevent formation of a biofilm during production, or in the final bottled packaged formulation. In one embodiment, xylitol and citrus extract are combined to form a preservative system in the liquid of the present invention. In one embodiment, xylitol is added from about 0.05 percent to about 5 percent by weight of the composition, e.g., from about 0.2 percent to about 1.5 percent by weight of the composition.

In one embodiment the citrus extract may be combined with a paraben preservative, which allows for the use of a lower level the paraben as compared to a formula without the citrus extract.

It is known that the combination of xylitol and sorbitol decreases bacteria metabolism and consequently decreases bacterial development. It is know that the xylitol has good activity against Streptococci. It has been used in oral care products due to its activity against S. mutans and biofilm formation Excipients that improve flavor and/or taste of the antacid composition and/or that enhance the antimicrobial activity may also be employed.

A maximum, a medium and a minimum concentration of the potential preservatives were each combined with other pharmaceutical excipients and assessed. An antacid composition containing citrus extract was determined to have superior properties.

An acid, such as citric acid, may be used in the formulation if pH adjustment is required. If used, the acid should not affect the antacid's mechanism of action or the effectiveness of the proposed preservative. According to an embodiment, the pH of the suspension is about 7-9.

The liquid antacid composition of the invention has advantages, including, e.g.:
(1) it maintains antimicrobial activity in an alkaline pH environment;
(2) its components do not undergo hydrolysis throughout the entire shelf life;
(3) it passes the challenge tests according USP criteria.
(4) it contains natural components which helps the microbiology integrity of the system is a natural product (5) it is effective against gram positive and negative bacteria, yeasts and molds;
(6) some components are GRAS (generally recognized as safe—21 C.F.R. § 170.30); and
(7) some components are certified by U.S. FDA as raw material secure for ingestion.

It is known to employ citrus extract in consumer products, e.g., WO1998014200 to Jones discloses the use of materials derived from citrus plants to produce or maintain weight loss.

WO2001045725 to Ancile Pharmaceuticals, Inc. discloses the use of plant extract, including citrus extract, to treat inflammatory bowel disease.

US20100323043 to Sorbent Technologies, Inc. discloses antimicrobial compositions that contain water, ethanol, a citrus extract and a surfactant, and their use to clean and/or protect the surface of objects.

U.S. Pat. No. 8,859,018 to Nestec S. A. discloses the use of antimicrobial essential oils in food and beverage compositions.

WO2014060990 to Bertoli discloses a method for preparing preservative for the food industry.

U.S. Published Applications Nos. 20120100231 and 20100323043 to Sorbent Technologies, Inc. disclose antimicrobial (e.g., moldicide, fungicide, bactericide, and virucide) compositions and their use to coat various surfaces to provide a lasting antimicrobial and antiviral effect.

U.S. Published Application No. 20060216246 to BioEnvelop Agro Inc. discloses the use of an aqueous oral gel containing food-grade ingredients to protect or isolate soft tissue of the oral cavity, or teeth, during a dental procedure such as tooth whitening.

U.S. Published Application No. 20140322147 to The Trustees of Columbia University in the City of New York discloses the use of a citrus extract such as 440D Foodgard® from Biosecur® in combination with benzyl alcohol and one or more additional agents selected from lauroyl arginate/ glyceryl laurate and essential oils or constituents thereof such as galangal oil, thyme oil, thymol, cinnamon leaf oil, cinnamon bark oil, lemongrass oil, orange oil, pine oil, cedarwood oil, curry leaf oil, and rosemary oil, as natural preservatives for personal care products, foods, beverages, and as topical or surface disinfectants.

All patent applications, patents, and other publications cited herein are incorporated by reference in their entirety.

There remains a need for a method of preserving antacid liquid compositions that would also result in a pleasant tasting product.

DETAILED DESCRIPTION

The present invention is directed to an antacid composition that contains a preservative system that does not breakdown when submitted to challenge tests throughout its shelf life.

The invention relates in particular to liquid antacid compositions comprising an effective amount of an antacid, a citrus extract, and optionally, one or more other pharmaceutically acceptable excipients. Preferably, the preparation contains aluminum hydroxide, magnesium hydroxide and/or calcium carbonate. In other embodiments, the preparation may include sodium bicarbonate and/or magnesium oxide. Preferably, the preparation contains 20-50 mg/5 ml of hydroxides and 5-40 mg/5 ml antacid of antifoam agent and of citrus extract A citrus extract that may be used in accordance with the invention is a water-soluble extract of citrus fruits, C.

*aurantium amara* (CAS 72968-50-4), *creticulata* (CAS 84929-38-4), and *csinensis* (CAS 8028-48-6). The final product, which contains ascorbic acid, glycerin, protein, and polyphenols is manufactured using a combination of citric fruits. All ingredients used to manufacture the *citrus* extract are food grade and GRAS for their intended uses.

Flavonoids (or bioflavonoids) (from the Latin word flavus meaning yellow, their color in nature) are a class of plant secondary metabolites. Chemically, they have the general structure of a 15-carbon skeleton, which consists of two phenyl rings (A and B) and heterocyclic ring (C).

Flavonoids have been shown to have a wide range of biological and pharmacological activities in in vitro studies. Examples include anti-allergic, anti-inflammatory, antioxidant, anti-microbial (antibacterial, antifungal, and antiviral, anti-cancer, and anti-diarrheal activities.

Research at the Linus Pauling Institute and the European Food Safety Authority shows that flavonoids are poorly absorbed in the human body (less than 5%), with most of what is absorbed being quickly metabolized and excreted.

The *citrus* flavonoids include hesperidin (a glycoside of the flavanone hesperetin), quercitrin, rutin (two glycosides of the flavonol quercetin), and the flavone tangeritin.

Flavonoids can function as direct antioxidants and free radical scavengers, and have the capacity to modulate enzymatic activities and inhibit cell proliferation. In plants, they appear to play a defensive role against invading pathogens, including bacteria, fungi and viruses. The peel of *citrus* fruits is a rich source of flavonoids. Citrus flavonoids have a large spectrum of biological activity and have been documented to possess antibacterial activity against a wide range of Gram-negative bacteria.

In addition, a pH adjusting agent may be added in an amount to bring the pH of the preparation to a desired level.

The composition according to the invention, in unit dosage form, may be administered, for example, 2-4 times per day. The dosage will depend on the active agents that are employed, the condition being treated and the age and weight of the patient. Typical dosages include about 10-20 ml of the preparation containing the dose of antacid selected to achieve the desired acid neutralizing effect. A suitable dose range for antacid is about 100 to about 2000 mg. Dosages from about 5 mL up to about 60 mL a day may be employed. 60 mL=9600 mg hydroxides.

The liquid compositions of the invention are aqueous suspensions containing the active ingredients in admixture with pharmaceutically acceptable excipients typically found in aqueous suspensions for oral administration. Such excipients may be suitable suspending agents, for example, propylene glycol, sodium alginate, polyvinylpyrrolidone, gum tragacanth, gum acacia, xanthan gum, locust bean gum and cellulose derivatives such as sodium carboxymethylcellulose, microcrystalline cellulose, hydroxy ethylcellulose, methyl cellulose or hydroxypropyl methylcellulose or mixtures thereof. Also included may be dispersing or wetting agents such as sorbitan esters or lecithin, antigelling additives, surface modifiers, aqueous or non-aqueous vehicles such as sorbitol solution, ethyl alcohol or fractionated vegetable oils, or solvents.

The compositions may also contain flavorings, colorants and/or sweeteners as appropriate. Suitable flavorants include fruit flavors, peppermint, licorice or bubble gum flavors. The sweetening agents may be for example bulk sweeteners or polyols (e.g., maltitol, sorbitol) and/or intense sweeteners such as saccharin, aspartame or acesulfame K.

Other active agents may be added to the preparation. For instance, antiflatulents, analgesics, antidiarrheals, $H_2$ receptor antagonists like cimetidine, ranitidine, nizatidine or famotidine, proton pump inhibitors such as omeprazole and lansoprazole, antispasmodic agents or anti-foaming agents like simethicone may be added as well as other gastrointestinal agents in dosage amounts conventionally used in the treatment of gastrointestinal dysfunction.

Histamine H2 receptor antagonists are agents which reduce acid secretion and are effective in the treatment of many gastric disorders. Co-administration of histamine H2 receptor antagonists and an antacid is known for example from U.S. Pat. No. 5,229,137 and International Application No. WO9200102. A typical preparation may contain about 100 mg to about 400 mg of cimetidine, or 50 mg to about 150 mg of ranitidine or 10 mg to 40 mg of famotidine per dosage unit (e.g., per 5 ml). Typically, the histamine H2 receptor antagonist is employed as the free base or, in the form of the physiologically acceptable salt, such as the hydrochloride salt in the case of ranitidine.

Racecadotril, dexecadotril and ecadotril are antidiarrheal drugs which acts as an enkephalinase inhibitor. A typical preparation may contain about 10 mg to about 200 mg racecadotril, dexecadotril and/or ecadotril.

The liquid antacid compositions of the present invention may be prepared according to conventional techniques well known in the pharmaceutical industry. Thus, for example, the antacid and the *citrus* extract may be admixed, if desired, with suitable excipients and dispersed in an aqueous vehicle.

As stated, the use of *citrus* extract in an antacid composition provides for superior resistance to microbial growth without compromising the acid neutralizing capacity of the antacid. Additionally, since high amounts of preservatives such as parabens are not required the taste of the finished product is greatly improved over the prior art. Additionally, the expected shelf life of the product may be increased over current commercially antacid suspensions.

The invention may be further illustrated by the following examples, which are provided to illustrate, but not limit the scope of the invention.

Example 1

Liquid Antacid Compositions

Liquid antacid compositions are prepared as follows:

In a suitable preparation vessel such as a clean stainless steel vessel, solvent and proposed preservative are added and mixed. An antacid basis (aluminum hydroxide, magnesium hydroxide, sorbitol and a small amount of parabens is then added and mixed. Simethicone and flavor may then be added and the mixture is stirred. The suspension is then milled, pasteurized at specified temperature and filled into bottles.

Microbiology Criteria

Antimicrobial Effectiveness Testing

The antacid compositions were tested for resistance to microbial growth in accordance with procedures including those established by the Brazilian Pharmacopeia and the US Pharmacopoeia using the USP standard organisms.

According to the test requirements the test results should meet the following requirements:
(1) USP NF 37—Category 4—Antacids: no increase from the initial calculated count at 14 and 28 days for bacteria, yeast and molds.

Organic Citrus Extract

The challenge test results were satisfactory for all three tested concentrations (0.5%, 1.0% and 1.9%) of organic *citrus* extract. No traces of formaldehyde or other synthetic preservatives were found.

1) Results

In all formulas containing *citrus* extract (0.025% to 1.90%) tested, as well as a combination of *citrus* extract with xylitol.

TABLE 12

2) Formula Comparison

Current Antacid Formula (mg/ml)

| | |
|---|---|
| Aluminum Hydroxide | 80.000 |
| Magnesium Hydroxide | 80.000 |
| Simethicone | 6.000 |
| Dye/Colorant* | 0.04-0.06 |
| Artificial Flavor | 2.50-3.50 |
| Methylparaben | 1.70 |
| Propylparaben | 0.30 |
| Sodium Saccharin | 0.10-0.35 |
| Citric Acid | 0.200-0.300 |
| Purified Water | q.s.p |
| Sorbitol solution 70% | 45.00-60.00 |

New Antacid Formula (mg/ml)

| | |
|---|---|
| Aluminum Hydroxide | 80.000 |
| Magnesium Hydroxide | 80.000 |
| Simethicone | 6.000 |
| Dye/Colorant* | 0.04-0.06 |
| Artificial Flavor | 0.02-0.05 |
| Sodium Saccharin/Sucralose | 0.01-0.30 |
| *Citrus* Extract | 0.005-1.900 |
| Citric Acid | 0.200-0.300 |
| Purified Water | q.s.p |
| Sorbitol solution 70% | 45.00-60.00 |
| Parabens | 0.02-0.009 |

*If necessary addition

The use of the *citrus* extract permits reduced use of paraben concentration and thus reduced use of synthetic preservative.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

REFERENCES

1. MILGROM P., LY K. A., ROTHEN M., Research findings on xylitol and the development of xylitol vehicles to address public health needs, National Center for Biotechnology Information, NIH Public Access, Author Manuscript, available online on July 2009.
2. MÄKINEN K. M., EVA S., Effect of Xylitol on some Food-Spoilage Microorganisms, Journal of Food Science, 46:950-951, 2006.
3. SODERLING E., HIRVONEN A., KARJALAINEN S., FONTANA M., CATT D., SEPPA L., The effect of Xylitol on the composition of the oral flora: A Pilot Study, European Journal of Dentistry, Vol 5, January 201, Pages 24-31.
4. AKSOY A, NIZAMI D, KOKSAL F., In vitro and in vivo antimicrobial effects of mastic chewing gum against Streptococcus mutans and mutans streptococci, Archives of Oral Biology, Vol. 51, Issue 6, June 2006, Pages 47-481
5. CHEMYUNION QUÍMICA L tda., HEBEATOL: Aditivo multifunctional de origem vegetal
6. CHEMYUNION QUÍMICA L tda., HEBEATOL: Aditivo multifunctional de origem vegetal "free form"
7. ROWE. C. R., SHESKEY J. P., QUINN E. M., Handbook of Pharmaceutical Excipients, Sixth Edition, Pharmaceutical Press, 2009, ISBN 978-0-85369-792-3
8. COSTERTON, J. W.; LEWANDOWSKI, Z.; CALDWELL, D. E.; KORBER, D. R.; LAPPIN-SCOTT, H. M. Microbial Biofilms. Ann. Rev. Microbiol, v. 49.p. 711-745, 1995.
9. KATSUYAMA M, MASAKO K, ICHIKAWA H, et al. A novel method to control the balance of skin microflora. Part 1. Attack on biofilm of Staphylococcus aureus without antibiotics, J Dermatol Sci 2005; 38(3):197-205.
10. "Safety assessment of esters of p-hydroxybenzoic acid (parabens)", M. G. Soni, I. G. Carabin, G. A. Burdock, Food and Chemical Toxicology 43 (2005) 985-1015
11. United States Environmental Protection Agency http://www.epa.gov/airtoxics/hlthef/phenol.html.

The invention claimed is:

1. A liquid antacid composition comprising:
   a) an antacid, wherein said antacid is selected from the group consisting of aluminum hydroxide; calcium hydroxide; magnesium hydroxide, sodium bicarbonate, and magnesium oxide;
   b) about 0.025 mg/ml to about 1.9 mg/ml of a *citrus* extract, wherein the *citrus* extract comprises *citrus aurantium amara* (CAS 72968-50-4), *citrus reticulata* (CAS 84929-38-4), and *citrus sinesis* (CAS 8028-48-6);
   c) xylitol; and
   d) optionally, one or more other pharmaceutically acceptable excipients;
   wherein said liquid antacid composition meets the requirements of USP NF 37—category 4-antacids: no increase from the initial calculated count at 14 and 28 days for bacteria, yeast and molds;
   wherein the pH of the composition is about 7 to about 9.

2. The liquid antacid composition of claim 1, wherein the antacid is magnesium hydroxide.

3. The liquid antacid composition of claim 1, wherein the antacid is aluminum hydroxide.

4. A method for neutralizing excess stomach acid in a human or lower animal, comprising orally administering to said human or lower animal an effective amount of the liquid antacid composition of claim 1.

5. A method for the treatment of a gastrointestinal disorder in a human or lower animal, comprising administering to said human or lower animal an effective amount of the liquid antacid composition of claim 1.

6. The method of claim 5 wherein the gastrointestinal disorder is selected from the group consisting of acid indigestion, heartburn, dyspepsia, sour stomach, reflux esophagitis, hiatal hernia and flatulence symptoms.

7. The liquid antacid composition of claim 1, further comprising a preservative selected from the group consisting of butylparaben, methylparaben and propylparaben.

8. The liquid antacid composition of claim 1, further comprising a pharmaceutically effective amount of a histamine H2 receptor antagonist.

9. The liquid antacid composition of claim 8, wherein the histamine H2 receptor antagonist is selected from the group consisting of cimetidine, ranitidine, nizatidine and famotidine.

10. The liquid antacid composition of claim 1, further comprising sorbitol.

11. The liquid antacid composition of claim 1, further comprising simethicone.

* * * * *